United States Patent [19]

Sipe et al.

[11] Patent Number: 4,816,388
[45] Date of Patent: Mar. 28, 1989

[54] HUMAN PREALBUMIN AND RELATED METHODS AND PRODUCTS

[75] Inventors: Jean D. Sipe, Roslindale; Alexander S. Whitehead, Needham; Alan S. Cohen, Newton; Martha Skinner, Chestnut Hill, all of Mass.

[73] Assignee: Children's Medical Center Corporation, Boston, Mass.

[21] Appl. No.: 792,817

[22] Filed: Oct. 30, 1985

[51] Int. Cl.⁴ .................. C12Q 1/68; C07H 15/12; C12N 15/00

[52] U.S. Cl. ........................... 435/6; 435/68; 435/172.3; 435/320; 435/803; 435/252.33; 436/808; 436/811; 536/27; 935/11; 935/29; 935/78; 935/80

[58] Field of Search ............... 435/6, 68, 172.3, 253, 435/317, 803, 810; 436/501, 808, 811; 536/27; 935/2, 4, 11, 29, 73, 78, 80

[56] References Cited

U.S. PATENT DOCUMENTS 4,395,486  7/1983  Wilson et al. ................... 435/6
4,517,294  5/1985  Bock et al. ..................... 935/11 X

OTHER PUBLICATIONS

Sasaki, H., et al., "Diagnosis of Familial Amyloidotic...", Biochem, Biophys. Res. Comm. 125 (2), 636-642 (12/14/84).
Wallace, M. R. et al., "Localization of the Human Prealbumin Gene", Biochem. Biophys. Res. Comm. 129 (3), 753-758 (6/28/85).
Tzuzuke, T., et al., "Structure of the Human Prealbumin Gene", J. Biol. Chem. 260 (22), 12224-12227 (10/5/85).
Benson, M. D., et al., J. Clin. Invest. (1985) 75:71-75.
Whitehead et al., Mol. Biol. Med. (1985) 7: in Press.
Wallace et al., Clin. Res. (1985) 33:592A.
Nakazato, M. et al., The Lancet (1985) 1:99.
Mita, S. et al., Biochemical and Biophysical Research Coomunications Academic Press, Inc., vol. 124, No. 2, 1984, pp. 558-564.

Primary Examiner—Robert J. Warden
Assistant Examiner—Richard Wagner
Attorney, Agent, or Firm—David G. Conlin; Linda M. Buckley

[57] ABSTRACT

Recombinant human prealbumin and a method for producing such human prealbumin through recombinant DNA techniques including preparation and isolation of a cDNA sequence coding for human prealbumin, construction of a cloning vector and an expression vector containing said cDNA sequence, and expression of human prealbumin in a prokaryotic cell transformed by said expression vector are disclosed. The invention further relates to the use of human prealbumin cDNA in the diagnosis by hybridization methodologies of medical conditions with which variant forms of prealbumin are associated. Also disclosed is a method for diagnosing some Type I familial amyloid polyneuropathies by a restriction endonuclease assay with an enzyme which recognizes the nucleotide base sequence 5'-ATGCAT-3'.

12 Claims, 2 Drawing Sheets

FAMILY 1 PEDIGREE

FAMILY 1 PEDIGREE

SOUTHERN BLOT ANALYSIS

HUMAN PREALBUMIN AND RELATED METHODS AND PRODUCTS

FIELD OF THE INVENTION

This invention relates to human prealbumin, to the production of human prealbumin by recombinant DNA techniques, including preparation and isolation of cDNA coding for human prealbumin and particularly to the use of human prealbumin cDNA in the diagnosis by hydridization methodologies of medical conditions in which variant forms of prealbumin have been implicated. The invention further relates to the expression of recombinant DNA to produce human prealbumin, to expression vectors useful for expressing human prealbumin, to microorganisms and cell lines transformed with said vectors, and to methods for producing human prealbumin by recombinant DNA techniques.

BACKGROUND OF THE INVENTION

The familial amyloid polyneuropathies (FAPs) are systemic amylid syndromes which are inherited in an autosomal dominant fashion (Glenner, G. G. et al., *The Metabolic Basis of Inherited Disease* pp 1308-1339, McGraw-Hill, New York 1978). They are characterized by the deposition of fibrils containing the plasma protein prealbumin (transthyretin) (Costam, P. P. et al., *Proc. Natl. Acad. Sci., USA* (1978) 75:4499; Benson, M. D., *J. Clin. Invest.* (1981); 67: 1035; and Skinner, M. et al., *Biochem. Biophys. Res. Comm.* (1981) 99: 1326.). Prealbumin is a 55 K Mr protein, composed of four identical subunits, which is involved in thyroid hormone and vitamin A transport (Blake, C.C.F., Proc. R. Soc. Lond. (1981) B211: 413.) Recently prealbumin isolated from the amyloid deposits of FAP patients has been sequenced and shown to have various single amino acid substitutions not found in the circulating prealbumin of normal individuals. One FAP associated prealbumin variant has a methionine for valine substitution at amino acid 30 and is found in kinships of Portuguese (Saraiva, M. J. M. et al., *J. Clin. Invest* (1984) 74: 104), Japanese (Tawara, S. et al., *Biochem. Biophys. Res. Comm.* (1983) 116: 880) and Swedish (Dwulet, et al., *Proc. Natl. Acad. Sci., USA* (1984) 81: 694; and Whitehead, A. S. et al., *Mol. Biol. Med.* (1985) Vol. 7 in press) ancestry type 1 (FAP). This prealbumin variant is present in the plasma of some kinships afflicted with type 1 FAP and it has been proposed that peptide mapping would provide a definitive diagnostic test for this form of the disease (Saraiva, M. J. M. et al., supra; Benson, M. D. et al., J. Clin. Invest. (1985) 75: 71.) Another type 1 FAP associated prealbumin variant has been identified by Whitehead et al., *Mol. Biol. Med.* supra. The variant prealbumin allele associated with type 2 FAP has a serine for isoleucine substitution at position 84 (Wallace et al., *Clin. Res.* (1985) 33: 592A). Variant prealbumin alleles have also been implicated in Alzheimers Disease (Shirahama, T. et al., *Am. J. Pathol.* (1982) 107: 41; A. S. Cohen and J. Sipe, NIH Grant No. P50-AG/NH05141 original submitted 3/19/84, revised 11/07/84).

There are three basic methods currently in use for detecting variant protein alleles: detecting the altered protein molecule itself; determining the nucleotide sequence of the coding regions of the variant gene; and detecting mutations that affect Southern blot hydridization patterns arising from either insertions or deletions in the gene or point mutations which either create or destroy restriction endonuclease recognition sequences.

The method described by Benson et al. for detecting carriers of the Met 30 human prealbumin variant falls into the first of the basic methods described. (Benson, M. D. et al., supra.) Since normal prealbumin has only one methionine (position 13), treatment with cyanogen bromide (CNBr), which cleaves only at methionines, results in two peptides. CNBr treatment of the Met 30 variant gives three peptides. The extra peptide is detected by high performance liquid chromatography (HPLC) or sequential Edman degradation.

Nakazato et al. report a radioimmunossay for the Met 30 variant of human prealbumin based on a nonapeptide (position 22-30) of the prealbumin variant. (Nakagato, M. et al., *The Lancet* (1985) 1: 99).

The second approach described above to determine the DNA structure of the mutant gene is a long and labor intensive process requiring cloning of normal and variant alleles. As such there is not much interest in this approach.

In order to detect variant prealbumin alleles by the third approach described above, use of restriction endonuclease based assays, it is necessary to clone and sequence cDNA for the prealbumin variant of interest. Recent advances in biochemistry and in recombinant DNA technology have made it possible to clone DNA and to achieve the controlled synthesis of specific proteins using the technique of molecular cloning. Molecular cloning involves isolating and purifying a nucleotide sequence coding for a particular protein, inserting the sequence into a plasmid or other cloning vehicle and transferring the cloned gene to a suitable cell for amplification and/or expression of the protein. Maniatis, T. et al.—*Molecular Cloning—A Laboratory Manual,* Cold Spring Harbor Laboratory, Cold Spring Harbor, New York, 1982. The protein can then be isolated and purified by conventional techniques.

Restriction endonucleases are enzymes, isolated primarily from prokaryotes, which recognize specific nucleotide sequences within a DNA molecule (Maniatis et al., supra, at pp 98-106). Generally, restriction endonucleases may be classified into three groups. Type-I and type-III enzymes carry methylase and an ATP-requiring cleavage activity in the same protein. Both types of this enzyme recognize unmethylated sequences in a substrate, but type-I enzymes cleave randomly, while type-III enzymes cleave at specific sites. Type-II restriction enzymes consist of a separate restriction endonuclease and modification methylase. A large number of type-II enzymes have been isolated (Roberts, R. J. *Nuc. Acids Res.* (1982) 10:R117), many of which are useful in molecular cloning. These enzymes cut DNA within or near a particular recognition sequence, which typically is from four to six nucleotides in length. In general, different restriction enzymes recognize different target nucleotide sequences. However, there are several enzymes isolated from different sources which recognize the same target sequences. These enzymes are known as isochizomers. Most restriction enzymes recognize either tetranucleotide, pentanucleotide or hexanucleotide sequences; see Roberts, R. J., *Nuc. Acids Res.* (1983) 11:R135.

A restriction endonuclease has been employed in an assay for detecting the sickle cell allele (beta$^S$ gene) (Wilson et al., U.S. Pat. No. 4,395,486). Wilson et al. analyzed amniotic fluid by isolating DNA therefrom, digesting the DNA with the restriction enzyme Dde I, which recognizes the nucleotide base sequence CTNAG, and separating the DNA fragments following cleavage. Using standard hybridization probe detection methods and a specific probe for the human beta-globin gene, the presence of an approximately 376 base pair fragment and the absence of an approximately 175 base pair fragment in the analyte was stated to be indicative of the presence of the sickle cell genotype.

It would be advantageous to develop diagnostic tests for medical conditions associated with variant prealbumin alleles using hybridization based assays. Moreover, it is desirable to have a recombinant source of human prealbumin that can supply normal prealbumin protein substantially free of other proteins of human origin. Thus, there is much interest in cloning cDNA for human prealbumin in quantities and purity sufficient for use in clinical applications.

SUMMARY OF THE INVENTION

The present invention provides recombinant human prealbumin and a means or method for producing such prealbumin through recombinant DNA techniques including (1) preparation and isolation of cDNA sequences coding for prealbumin, (2) construction of expression vectors containing said cDNA sequences, and (3) expression of prealbumin in a prokaryotic cell transformed by said expression vector. The present invention also provides the use of human prealbumin cDNA in the diagnosis, by use of hybridization methodologies, of medical conditions in which variant forms of prealbumin have been implicated.

DETAILED DESCRIPTION OF THE INVENTION

Figure 1:
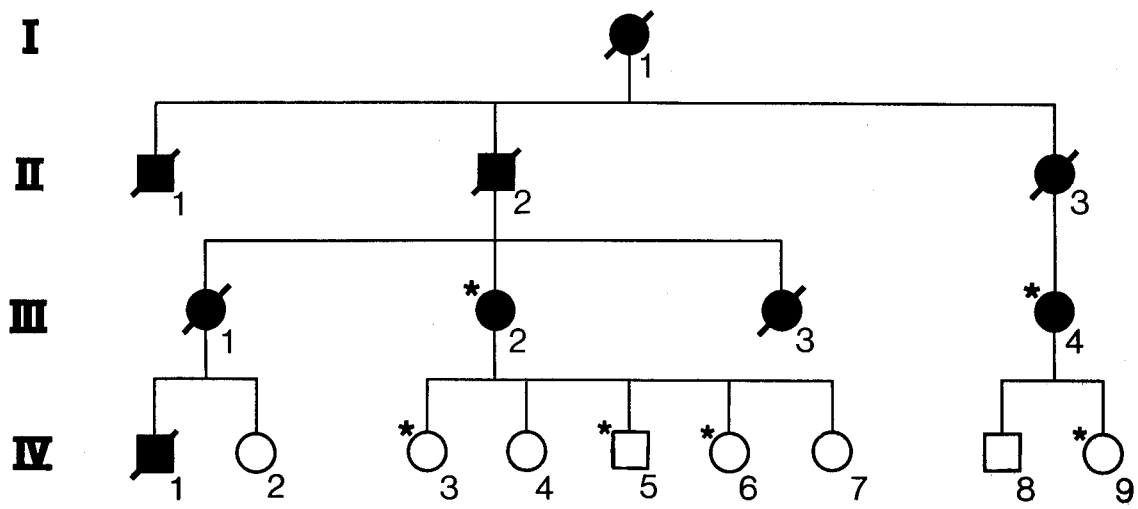
FIG. 1 illustrates the pedigree of Family 1. Squares denote males, circles females. Shaded symbols indicate individuals clinically diagnosed as having Type I FAP or, in the case of deceased individuals from prior generations, where medical records or family information support such diagnosis. Slashed symbols indicate deceased individuals; age at death was as follows - I1: 50 years, II1,2 and 3: 50, 41 and 40 years respectively: III1 and 3: 53 and 50 years respectively: IV1: 34 years. Living individuals whose DNA exhibits a variant prealbumin pattern are indicated by an asterisk. For the purposes of confidentiality only relevant members of this large pedigree are included.

The following definitions are supplied in order to facilitate the understanding of this case. To the extent that the definitions vary from meaning circulating within the art, the definitions below are to control.

Amplification means the process by which cells produce gene repeats within their chromosomal DNA.

An enhancer is a nucleotide sequence that can potentiate the transcription of a gene independent of the position of the enhancer in relation ot the gene or the orientation of the sequence.

A gene is a deoxyribonucleotide sequence coding for a given protein. For the purposes herein, a gene shall not include untranslated flanking regions such as RNA transcription initiation signals, polyadenylation addition sites, promoters or enhancers.

Orientation refers to the order of nucleotides in a DNA sequence. An inverted orientation of a DNA sequence is one in which the 5-prime to 3-prime order of the sequence in relation to another sequence is reversed when compared to a point of reference in the DNA from which the sequence was obtained. Such points of reference can include the direction of transcription of other specified DNA sequences in the source DNA or the origin of replication of replicable vectors containing the sequence.

Transcription means the synthesis of RNA from a DNA template.

Transformation means changing a cell's genotype by the cellular uptake of exogenous DNA. Transformation may be detected in some cases by an alteration in cell phenotype. Transformed cells are called transformants.

Translation means the synthesis of a polypeptide from messenger RNA.

As used herein the term "recombinant human prealbumin" refers to human prealbumin expressed in transferred cells.

The patent and scientific literature is replete with processes useful for the production of recombinant products. Generally, these techniques involve the isolation or synthesis of a desired gene sequence, and the expression of that sequence in either a procaryotic or eucaryotic cell, using techniques well known to the skilled artisan. Once a given gene has been isolated, purified and inserted into a transfer vector (i.e., cloned), its availability in substantial quantity has typically been assured. The vector with the cloned gene is transferred to a suitable microorganism or cell line, for example, bacteria, yeast, mammalian cell lines such as COS (monkey kidney) and CHO (Chinese hamster ovary), insect cell lines, and the like, wherein the vector replicates as the microorganism or cell line proliferates and from which the vector can be isolated by conventional means. Thus there is provided a continuously renewable source of the gene for further manipulation, modification and transfer to other vectors or other loci within the same vector.

Expression can be obtained by transferring the cloned gene, in proper orientation and reading frame, into an appropriate site in an expression vector such that translational read-through from a procaryotic or eucaryotic gene results in synthesis of a protein precursor comprising the amino acid sequence coded by the cloned gene including or linked to Met or an amino-terminal sequence from the procaryotic or eucaryotic gene. Vectors used for eukaryotic cell expression typically contain various elements such as enhancers, promoters, introns, polyadenylation sites, 3-prime and 5-prime noncoding regions and translational activators. A variety of specific protein cleavage techniques may be used to cleave the protein leader, if produced, at a desired point so as to release the desired mature amino acid sequence, which can then be purified by conventional means. In some cases, the mature protein containing the desired amino acid sequence is produced without the need for specific cleavage techniques and may also be released from the cells into the extracellular growth medium.

Prealbumin specific cDNA clones have been isolated from an adult human liver library. An oligonucleotide mixture (5' TTPy-CAPy-GAu-CaPy-GCX-GA 3') based on the prealbumin amino acid sequence between residues 87 and 92 was used to screen 40,000 recombinant colonies of an adult human liver cDNA library by established procedures (Woods, D. E. et al., *Proc. Natl. Acad. Sci. USA* (1982) 79: 5661). Approximately fifty positive clones were identified and eight were selected for further study. Nucleotide sequence analysis obtained by the dideoxy chain termination method (Sanger, F. et al., *Proc. Natl. Acad. Sci. USA* (1977) 74: 5463) and hybridization analysis confirmed that these clones were complementary to prealbumin. The largest clone, pTTR3 (approximately 600 bp), spans the codons specifying amino acids 30 and 31 and was used in subsequent experiments.

Nsi1 digested DNA from normal individuals and type 1 FAP patients kown to have the methionine for valine substitution has been analyzed in Southern blot hybridization experiments and a variant pattern associated with the disease phenotype has been identified (Whitehead et al., *supra*). This variant pattern in which the nucleotide sequence specifying amino acid residues 30 and 31 is such that a methionine substituted for a valine at position 30 creates a new Nsi1 restriction endonuclease recognition site in the gene encoding the variant product. This variant pattern permits direct identification of individuals carrying this disease-associated prealbumin allele and will facilitate diagnosis prior to clinical presentation, genetic counselling and renatal screening procedures in some families with type 1 FAP.

A number of FAP patients whose amyloid deposits contain a variant prealbumin molecule other than that with the methionine for valine substitution have been described above. Although the above analysis based on a new Nsi1 site is not applicable to FAP kinships whose disease is in association with other amino acid substitutions of prealbumin, the normal prealbumin clone, pTTR3, may be used in analysis of any variant prealbumin using appropriate restriction endonucleases. Prealbumin specific cDNA clones according to the present invention have been used to localize the prealbumin gene to human chromosome 18 (Whitehead et al., supra.).

A human prealbumin specific cDNA clone, pTTR3, was used to analyze DNA samples from several patients with familial amyloid polyneuropathy. In classical type 1 FAP a variant prealbumin molecule with a methionine for valine substitution at position 30 has been implicated in the pathogenesis of this autosomal dominant condition. The codon for methionine is AUG, therefore the variant ellele would be expected to contain the nucleotide sequence ATGCAT specifying amino acids 30 and 31. ATGCAT is the recognition sequence for the restriction endonuclease Nsi1. In Southern blot hybridization experiments the prealbumin clone, pTTR3, detects Nsi1 DNA fragments of 6.5 Kb and 3.1 Kb in normal individuals. In a family known to have the methionine for valine substitution (Family 1, infra) 2 individuals with Type 1 FAP were shown to have novel bands of 4.9 Kb and 1.6 Kb which are derived from cleavage of the additional Nsi1 site in the region of the variant allele corresponding to the 6.5 Kb band in the normal allele. Of seven offspring subjected to similar analysis 4 were shown to have the variant prealbumin DNA patterns indicative of the presence of the FAP-associated allele. All offspring were younger than the usual age of onset of Type 1 FAP. The above analysis, therefore, allows diagnosis of FAP in members of this family prior to clinical presentation and forms a basis for genetic counselling and prenatal diagnosis in this and other similar families.

Prealbumin has been found associated with amyloid deposits in the peripheral nervous system (Costa et al., supra) and in the central nervous system in senile cerebral amyloid, Alzheimer's disease, (Shirahama, T. et al., supra) for which there is a familial form. In addition prealbumin amyloid fibrils occur in senile cardiac amyloidosis (Cornwall, G. G. et al., *Immun.* (1981) 44: 447.) and familial amyloid cardiomyopathy (Husby, G. et al. *Clin. Exp. Immunol.* (1985) 60: 207). There is no known function for prealbumin in the nervous system, however two carrier interactionshave been described for the circulating form. Prealbumin is involved with vitamin A (retinol) transport through its association with retinol binding protein and with transport of thyroid hormone through direct binding (RAZ, A. et al., *J. Biol. Chem.* (1969) 244: 3230.) The latter function may be compromised in familial euthyroid hyperthyroxinemia in which a variant prealbumin with an increased binding capacity for thyroxine has been described (Moses, A. C. et al., *N. Engl. J. Med.* (1982) 306: 966.) Clones for human prealbumin will therefore be of use in studying the genetic basis for the many autosomal dominant diseases, in addition to FAP, in which variant forms and activities of prealbumin are implicated.

Since all types of FAP and Alzheimer's disease usually are not manifest until after the child bearing years methods according to the present invention of identifying carriers of the gene provide a basis for diagnosis before clinical presentation, genetic counseling and prenatal screening.

In accord with the preferred embodiment of this invention, the vector, pKT218, utilized for the amplication of human prealbumin cDNA pTTR3 has been deposited and is available from the American Type Culture Collection as Deposit Number ATCC 53306.

EXAMPLES

Example I

Patients and Methods

FAP kinships: Family 1 (COhen, A. S. et al., in Glenner, G. G., et al., eds., *Amyloid and Amyloidosis*, pp 67–77, Excerpts Medica, Amsterdam, 1980) is of Swedish origin and has had a history of variably diagnosed neurological disorders for over 60 years. The amyloid involvement in this kinship is typical of type 1 FAP (Glenner et al., supra) and is characterized by severe sensory neuropathy beginning in the lower extremities. Patients exhibit some autonomic nervous system dysfunction, including incontinence, impotence, postural hypotension and nocturnal diarrhea. The age of onset is before 40 years and the most frequent cause of death is severe renal disease. Autopsy typically reveals extensive involvement of blood vessels throughout the body with particularly marked involvement of skin, nerves, gastrointestinal tract and kidney. The methionine for valine substitution in prealbumin was determined from amyloid fibrils isolated from thyroid tissue removed at autopsy from one individual in family 1. DNA samples from two maternal aunts diagnosed as having type 1 FAP and their offspring were analyzed.

Family 2 (Libbey, C. A. et al., *Am. J. Med.* (1984) 76: 18) is of German/English ancestry and by clinical criteria is classified as type 1 FAP. This kinship, however, differs in that onset is in the seventh decade and the clinical course is milder. Although histologic and immunohistochemical evidence has established that an amyloid fibril of prealbumin origin is present in diseased members of this family, sequence analysis on the isolated fibril has not been performed. DNA samples from 2 affected individuals whose disease has been apparent for several years were analyzed.

In addition one individual from a third kinship with classical type 1 FAP symptoms and age of onset (Skinner, M. and Cohen, A. S. unpublished) was also analyzed.

Example II

Amino Acid Sequence Analysis of Amyloid Fibrils

A 14,000 $M_r$ protein was isolated from amyloid laden thyroid tissue of individual IV-1 (FIG. 1) who died at age 34 of malnutrition. The sequence of the first twenty amino acid residues had previously been reported to be identical to normal prealbumin (Skinner et al., supra). In this study, sequence analysis was continued through residue 42 with identification of amino acids by high performance liquid chromatography and thin layer chromatography. When compared with normal prealbumin the only difference was at position 30 where methionine residues were found in addition to valine indicating that the amyloid fibrils were composed of a mixture of the normal and variant forms of prealbumin.

Example III

Isolation of Prealbumin Specific cDNA Clones

RNA was extracted from the liver of an organ donor who had sustained severe injuires in an automobile accident 36 hours prior to brain death (Woods et al., supra). Polyadenylated RNA-containing message for perealbumin was prepared and the enzyme reverse transcriptase was used to prepare a single stranded DNA complementary to the mRNAs. Formation of ds cDNA was catalyzed by DNA polymerase and the overhanging ends were removed by S1 nuclease. A poly C tail was added to the ds cDNA using terminal deoxynucleotydyl transferase. Then the tailed cDNA was inserted into the plasmid pKT218 at the Pst I restriction enzyme recognition site to which had been added a poly G tail. Plasmid and cDNA were annealed and used to transform *E. coli* MC1061.

Cultures of transformed bacteria were replica plated, a process by which duplicate copies of a master plate were grown, and used for filter colony hybridization (Grunstein et al., infra). After lysis of the colonies to denature DNA and baking of the single strands to nitrocellulose, the filters were hybridized with $^{32}P$ prealbumin specific oligonucleotide probes while the master plate was kept as a source of positive colonies.

A synthetic olignucleotide mixture comprising all 17-nucleotide DNA sequence that could code for the amino acid sequences of prealbumin between residues 87 and 92 was prepared by a solid-phase phosphodiester method using a library or dimer anions (Gait et al., *Nuc. Acids Res.* (1980) 8: 1081; Markham et al., *Nuc. Acids Res.* (1980) 8: 5193). To ensure the presence of the correct sequence, the mixtures contained 64 different oligonucleotides in order to cover the degrees of codon ambiguity for each region of 6 amino acids.

To identify prealbumin specific cDNA clones, the oligonucleotide mixture was radio-labeled with $^{32}P$ and used to screen 40,000 clones. Approximately 50 of them hybridized specifically with this mixture. The largest clone, pTTR3 (approximately 600 bp), spans the codons specifying amino acids 30 and 31.

Example IV

Expression of Human Prealbumin cDNA

Plasmid DNA is isolated from cultures of pTTR3 by the cleared lysate method of Clewell, D. B. et al., *Proc. Nat. Acad. Sci.* (1969) 62: 1159. A concentrated suspension of bacteria is lyzed by the action of lysozyme and SDS. The lysate is cleared by ultracentrifugation to pellet the cell debris and chromosomal DNA. Protein is removed by phenol/chloroform extraction. DNA is precipitated with ethanol, and redissolved in buffered saline and the supercoiled plasmid is recovered by ultracentrifugation on cesium chloride gradients (Clewell et al., supra). The prealbumin specific cDNA contained in pTTR3 is excised by PstI digestion and purified by agarose gel electrophoresis. (*Methods in Molecular Biology Vol.* 2, ed. J. M. Walker, Humama Press, Clifton, N.J. 1984). This dC-tailed double stranded cDNA is hybridized to PstI - digested, dG-tailed pBR322 and the resulting ampicillin sensitive recombinant plasmids are used to transform E. coli RRI made competent by treatment with $CaCl_2$ (Birch, H. E. et al., *Biochem. Intl.* (1983) 6:653; J. M. Walker, supra).

In situ colony hybridization is carried out as described for pTTR3 in Example III above. The colonies which are positive to the pTTR3 cDNA insert are screened with anti-prealbumin antibodies purified from whole antiserum to prealbumin by affinity chromatography (Sipe, J. D. et al., *J. Immunol.* (19769 116: 1151).

The *E. coli* expressing the pTTR3 cDNA insert, i.e. normal human prealbumin protein, are extracted with 7M guanidine hydrochloride (Lomedico, P. T., et al., (*Nature* (1984) 312: 458). Transformed E. coli are used as a control. The crude extract is concentrated by ammonium sulfate precipitation and is fractionated by gel filtration on Ultragel AcA54 (LKB Instruments, Inc., Gaithersburg, MD). The fractions containing prealbumin are pooled and applied to an anti-prealbumin immunosorbent column. The prealbumin is eluted with 4M KSCN. The presence of bacterial contaminants is assessed by chemical and functional (LPS) analysis of the control extract from nontransformed bacteria.

Example V

Somatic Cell Hybrids

Somatic cell hybrids were derived from fusions of hypoxanthine phosphoribosyl transferase deficient mouse RAG cells or hamster E36 cells with white blood cells or fibroblasts from 3 unrelated human individuals and have been described previously (Mantzouranis, E. C. et al., *J. Biol. Chem.* (1985) 260: 7752; and Bruns, G. A. P. et al., *Biochem. Genetics* (1979) 17: 1031.)

Example VI
Isolation and Analysis of Human, Rodent and Somatic Cell Hybrid DNA High Molecular weight DNA from human peripheral blood lymphocytes, the rodent cell lines RAG and E36 and somatic cell hybrids was prepared (Gross-Bellard, M. et al., *Eur. J. Bioch.* (1977) 36: 32). Following digestions with the restriction endonucleases Sac1 or Nsi1 (New England Biolabs), DNA was size fractionated by egarose gel electrophoresis, alkali denatured and transferred to nitrocellulose filters (Southern, E. M., *J. Mol. Biol.* (1975) 98: 503.) The resulting Southern blots were hybridized overnight under standard conditions (Jeffreys, A. J. et al., *Cell* (1977) 12: 429) with pTTR3 which had been radiolabeled by nick translation (Rigby, P. W. J. et al., *J. Mol. Biol.* (1977) 113: 237.) washed in 30 mM NaCl/3 mM Na citrate/0.1% SDS at 65° C. for one hour, dried and exposed to Kodak XAR5 film.

Example VII
Analysis of DNA from FAP patients

Figure 2:
FIG. 2 illustrates Southern blot hybridization of pTTR3 with NsiI digested DNA (10 micrograms) from FAP patients and members of a type 1 FAP kinship in which affected individuals carry the methionine for valine substitution at residue 30 of prealbumin. The first 10 tracks represent members of Family 1-IV2, III2, IV3, IV4, IV5, IV6, IV7, III4, IV8, IV9. Individuals III2 and III4 have been clinically diagnosed as having FAP. Tracks 11 and 12 represent affected individuals (brothers) from Family 2. Track 13 represents an individual (male) with classical Type 1 FAP symptoms and age of onset. Molecular weight markers were HindIII digested lambda phage.

The nucleotide sequence of human prealbumin specifies the codons GUG and CAU for amino acid residues 30 and 31 (valine and histidine). In type 1 FAP the valine at position 30 is replaced by a methionine. The codone specifying methionine is AUG, thus the substitution giving rise to the disease phenotype is probably derived from a single G to A mutation of the first nucleotide of the codon specifying amino acid 30. The coding sequence of the variant allele would therefore contain a novel ATGCAT Nsi1 restriction endonuclease recognition site not present in the normal allele. DNA from the peripheral blood lymphocytes of 15 unrelated individuals was digested with Nsi1 and subjected to Southern blot analysis using radiolabeled pTTR3 as a hybridization probe. In all cases two bands of 6.5 Kb and 3.1 Kb were observed (data not shown), the intensity of each being approximately 1:1. DNA from the peripheral blood lymphocytes of 10 members of a kinship (FIG. 1) with Type 1 FAP was subjected to similar analysis (FIG. 2). Amino acid sequencing of prealbumin deposited in the tissues of one member (IV1 deceased) of this kinship had previously established the presence of the methionine for valine substitution in the affected members of this family. Individuals III2 and III4 have had a classical type 1 FAP clinical course for several years. When digested with Nsi1 and hybridized with radiolabeled pTTR3 their DNA patterns (FIG. 2, tracks B and H) differ from those found in normal individuals; the ratio of the 6.5 Kb band to the 3.1 Kb band is approximately 1:2 and two new bands 4.9 Kb and 1.6 Kb are apparent. The relative intensity and sizes of these bands indicate that they are derived from a novel Nsi1 restriction site in the region of the variant prealbumin gene corresponding to the 6.5 Kb fragment of the normal allele. The DNA patterns of the 7 offspring of individuals III2 and III4 (IV3-7; Tracks 3-7; and IV8,9;, Tracks 9 and 10) show that in 4 cases the variant allele has been transmitted to the next generation. These individuals are younger than the typical age of onset of type 1 FAP and their clinical assessment reveals no disease state as yet.

Of interest is the analysis of DNA from two FAP patients of another kinship (FIG. 2, tracks 11 and 12). These individuals are from family 2 in which the symptoms presented during the course of the disease are similar, though not identical, to those of classical type 1 FAP patients. A significant difference is an age of onset of the disease towards the end of the sixth decade of life, about 20-30 years later than that of type 1 FAP. Nsi1 digested DNA samples from these individuals shows a "normal" pattern detected by radiolabeled pTTR3, indicating that their disease is not a result of the prealbumin variant characterized by the methionine for valine substitution. Similar analysis of an unrelated FAP patient (FIG. 2, track 13) with classical type 1 symptoms and age of onset also reveals a "normal" pattern, thereby establishing the heterogeneity of the underlying biochemical defect in type 1 FAP.

Example VIII
Chromosomal Localization of the Human Prealbumin Gene

Figure 3:
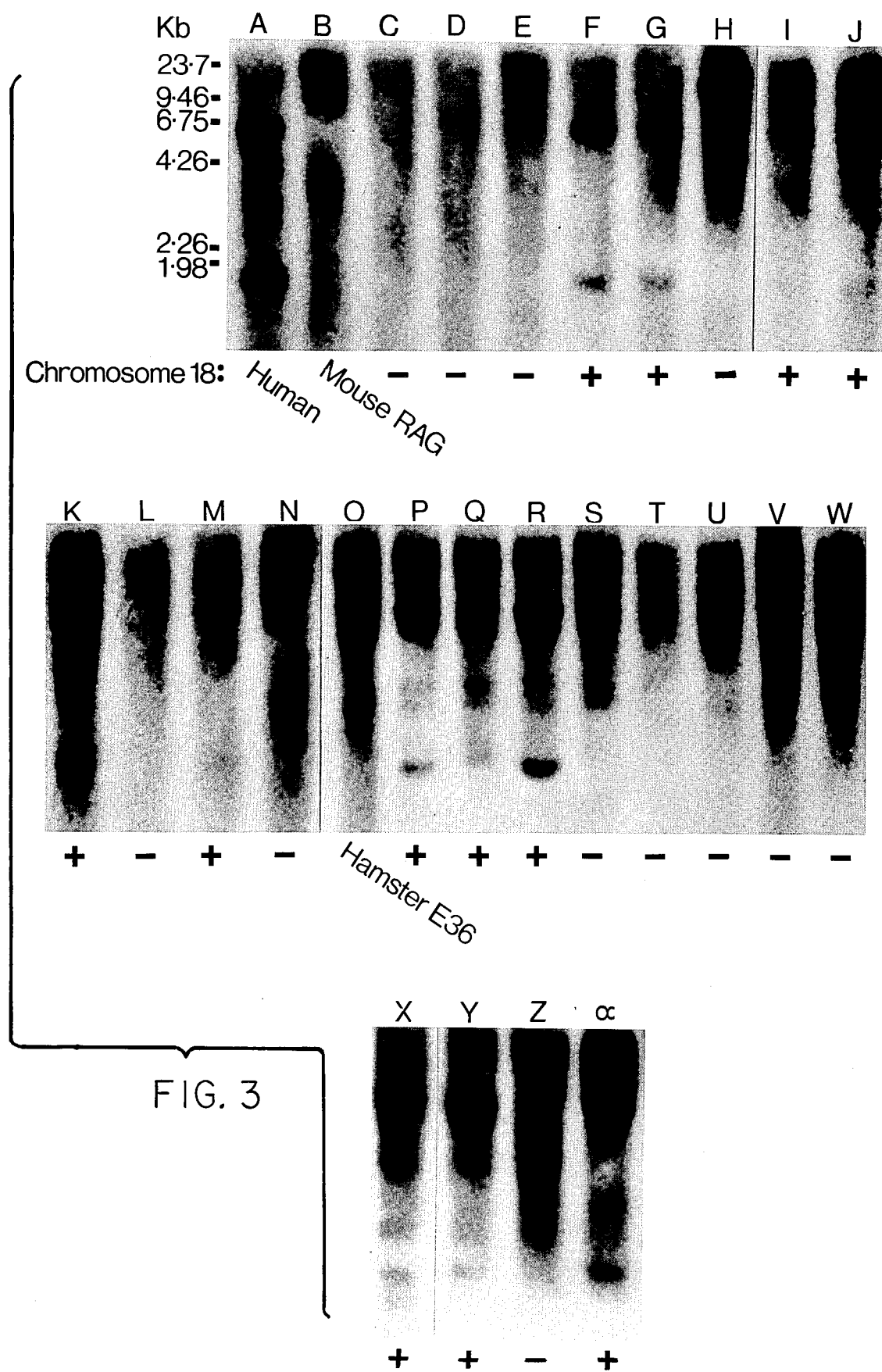
FIG. 3 illustrates Southern blot hybridization of pTTR3 with Sac1 digested DNA from mouse-human and hamster-human somatic cell hybrids (15 micrograms), the rodent parent cell lines (10 micrograms) and human peripheral blood lymphoctes (10 micrograms): Track A, human; Track B, mouse parent cell line RAG; Tracks C-N, mouse-human hybrids G24-A4, -B2, -B5, G17-4, -11, -17, -19, R3-6, -7, G46-C2; Track 0, hamster parent cell line E36; Tracks P to alpha, hamster-human hybrids G35-F3, -D2, -E3, -A2, -B5, -D3, -C5, -A4, -B4, -A5, -C2, -D5. Bands specific for the human prealbumin gene are at 5.6 Kb and 1.7 Kb. The presence or absence of human chromosome 18 is denoted below each track. Molecular weight markers were Hind III-digested lambda phage.

Somatic cell hybrids between human cells and mouse RAG or hamster E36 cells which have a full complement of rodent chromosomes and a limited but varied human chromosome content were analyzed for the presence or absence of the human prealbumin gene. DNA was isolated from 125 unrelated individuals, digested with the restriction endonuclease SacI, and subjected to Southern blot analysis using radiolabeled pTTR3 as a hybridization probe. Prealbumin specific bands of 5.6 Kb and 1.7 Kb, which were distinct from the mouse RAG or hamster E36 SacI restriction fragments, were identified (data not shown). DNA from 24 somatic cell hybrid lines was analyzed similarly and assessed for the presence or absence of the human prealbumin specific 5.6 Kb and 1.7 Kb bands (FIG. 3). The presence or absence of these bands correlates perfectly only with the presence or absence of chromosome 18 (Table 1 below) thereby allowing assignment of the prealbumin gene to human chromosome 18.

Table 1: Segregation of hybridization of the DNA probe pTTR3 to SacI-digested DNA from 24 somatic cell hybrids. Concordant: (++) probe hybridizes, chromosome present; (− −) probe does not hybridize, chromosome not present. Discordant: (+−) probe hybridizes, chromosome not present; (− +) probe does not hybridize, chromosome present. Data are summarized from hybridization of pTTR3 to DNA from aromatic cell hybrids (Mantzourani's, E. C. et al., supra and Burns et al., supra.) (FIG. 3) previously analyzed from human chromosome content. *Clones with chromosome present, in less than 15% of metaphases, or in which a chromosome specific isoenzyme of DNA probe exhibited only a weak signal were excluded from analysis for that chromosome. Clones with a rearranged chromosome were likewise excluded from the analysis.

TABLE 1

| Human Chromosome | HYBRIDATION OF TTR3 PROBE | | | | | |
|---|---|---|---|---|---|---|
| | Concordant | | Discordant | | Total | |
| | ++ | − − | +− | − + | Concordant | Discordant |
| 1* | 8 | 7 | 3 | 3 | 15 | 6 |
| 2* | 6 | 10 | 5 | 0 | 16 | 5 |
| 3* | 7 | 5 | 5 | 6 | 12 | 11 |
| 4* | 5 | 5 | 7 | 6 | 10 | 13 |
| 5 | 9 | 9 | 3 | 3 | 18 | 6 |
| 6 | 9 | 8 | 3 | 4 | 17 | 7 |

TABLE 1-continued

| Human Chromosome | HYBRIDATION OF TTR3 PROBE | | | | | |
|---|---|---|---|---|---|---|
| | Concordant | | Discordant | | Total | |
| | ++ | -- | +- | -+ | Concordant | Discordant |
| 7 | 9 | 6 | 3 | 6 | 15 | 9 |
| 8 | 5 | 7 | 7 | 5 | 12 | 12 |
| 9* | 3 | 7 | 8 | 4 | 10 | 12 |
| 10 | 10 | 5 | 2 | 7 | 15 | 9 |
| 11* | 9 | 8 | 3 | 3 | 17 | 6 |
| 12* | 10 | 8 | 2 | 3 | 18 | 5 |
| 13* | 5 | 5 | 4 | 6 | 10 | 10 |
| 14* | 8 | 3 | 4 | 8 | 11 | 12 |
| 15* | 6 | 8 | 6 | 3 | 14 | 9 |
| 16* | 7 | 5 | 3 | 7 | 12 | 10 |
| 17* | 4 | 9 | 6 | 3 | 13 | 9 |
| 18 | 12 | 12 | 0 | 0 | 24 | 0 |
| 19* | 9 | 2 | 1 | 9 | 11 | 10 |
| 20* | 9 | 7 | 3 | 4 | 16 | 7 |
| 21* | 7 | 4 | 5 | 7 | 11 | 12 |
| 22* | 8 | 3 | 4 | 8 | 11 | 12 |
| X | 12 | 0 | 0 | 12 | 12 | 12 |

Additional advantages and modifications of the invention disclosed herein will occur to those persons skilled in the art. Accordingly, the invention in its broader aspects is not limited to the specific details or illustrated examples described herein. Therefore, all departures made from the detail are deemed to be within the scope of the invention as defined by the appended claims.

What is claimed is:

1. Vector pTTR3 comprising a cDNA insert coding for a portion of human prealbumin protein.

2. A DNA sequence coding for human prealbumin protein substantially free of other human genes comprising the cDNA insert of claim 1.

3. A screening agent for identifying deoxyribonucleotide sequences and ribonucleotide sequences which encode for at least a portion of the human prealbumin gene the screening agent, comprising at least a portion of the cDNA insert of claim 1.

4. A screening agent for identifying deoxyribonucleotide sequences and ribonucleotide sequences which encode for at least a portion of the human prealbumin gene the screening agent, comprising the DNA sequence of claim 2.

5. A method for the diagnosis of conditions associated with variant forms of human prealbumin protein, the method comprising:
   (a) isolating DNA from human tissue;
   (b) digesting the DNA with a restriction endonuclease which recognizes the nucleotide sequence 5'-ATGCAT-3' present in the variant human prealbumin and absent in normal human prealbumin to form DNA fragments;
   (c) subjecting the digested DNA to size fractionation to form a pattern of the fragments;
   (d) hybridizing the fragments with cDNA, which cDNA encodes at least a portion of the normal human prealbumin gene and is capable of visualization; and
   (e) visualizing the pattern to determine the presence or absence of DNA fragments associated with the predetermined nucleotide sequence.

6. The method of claim 5 wherein the condition is selected from the group consisting of Alzheimers disease, familial amyloid polyneuropathy, and senile cardiac amyloidosis.

7. A method for the diagnosis of conditions associated with variant forms of human prealbumin protein, the method comprising:
   (a) isolating DNA from human tissue;
   (b) digesting the DNA with a restriction endonuclease which recognizes the nucleotide sequence 5'LATGCAT-3' present in the variant human prealbumin and absent in normal human prealbumin to form DNA fragments;
   (c) subjecting the digested DNA to size fractionation to form a pattern of the fragments;
   (d) hybridizing the fragments with the DNA of claim 2 the cDNA further being capable of visualization; and
   (e) visualizing the pattern to determine the presence or absence of DNA fragments associated with the predetermined nucleotide sequence.

8. A method for the diagnosis of Type I familial amyloid polyneuropathy associated with the substitution of meathionine for valine at amino acid position 30, the method comprising:
   (a) isolating DNA from human tissue;
   (b) digesting the DNA with a restriction endonuclease which recognizes the nucleotide sequence 5'-ATGCAT-3';
   (c) subjecting the digested DNA to Southern blot analysis using cDNA which encodes at least a portion of the normal human prealbumin gene as a hybridization probe and is capable of detection; and
   (d) detecting the presence of 4.9 Kb and 1.6 Kb bands.

9. The method of claim 8 wherein the restriction endonuclease is Nsi1.

10. A method for the diagnosis of Type I familial amyloid polyneuropathy associated with the substitution of methionine for valine at amino acid position 30, the method comprising:
    (a) isolating DNA from human tissue;
    (b) digesting the DNA with a restriction endonuclease which recognizes the nucleotide sequence 5'-ATGCAT-3';
    (c) subjecting the digested DNA to Southern blot analysis using the DNA of claim 2 the cDNA further being capable of visualization as a hybridization probe; and
    detecting the presence of 4.9 Kb and 1.6 Kb bands.

11. A diagnostic assay kit useful for identification of a particular medical condition associatted with variant forms of prealbumin by detecting a predetermined restriction enzyme cleavage site in a biological sample, said diagnostic kit comprising, in separate containers: a quantity of labeled normal human prealbumin cDNA capable of hybridizing with DNA fragments of the biological sample; and a quantity of restriction enzyme specific for said predetermined cleavage site.

12. A diagnostic assay kit useful for identification of a particular medical condition associated with variant forms of prealbumin by detecting a predetermined restriction enzyme cleavage site in a biological sample, said diagnostic kit comprising, in separate containers: a quantity of DNA according to claim 2, the cDNA being capable of hybridizing with DNA fragments of the biological sample and, being further capable of detection; and a quantity of restriction enzyme specific for said predetermined cleavage site.

* * * * *

UNITED STATES PATENT AND TRADEMARK OFFICE
CERTIFICATE OF CORRECTION

PATENT NO. : 4,816,388
DATED : March 28, 1989
INVENTOR(S) : Sipe et al.

It is certified that error appears in the above—identified patent and that said Letters Patent is hereby corrected as shown below:

On the title page:

In the Assignee designation, [73], an additional assignee should appear as follows:

Trustees of Boston University
Boston, Mass.

Signed and Sealed this

Seventeenth Day of July, 1990

*Attest:*

HARRY F. MANBECK, JR.

*Attesting Officer*        *Commissioner of Patents and Trademarks*